United States Patent [19]

Sasaki

[11] 4,297,874

[45] Nov. 3, 1981

[54] APPARATUS FOR MEASURING A PERCENTAGE OF MOISTURE AND WEIGHING OF A SHEET-LIKE OBJECT

[76] Inventor: Shinichi Sasaki, 5-17-19,, Tokiwa, Urawa-shi, Saitama-ken, Japan

[21] Appl. No.: 88,570

[22] Filed: Oct. 26, 1979

[51] Int. Cl.³ .................... G01G 7/00; G01N 27/06; G01R 27/00

[52] U.S. Cl. ................... 73/73; 177/210 FP; 324/58.56; 340/602; 340/665

[58] Field of Search ......... 73/73; 324/58.5 A, 58.5 C; 162/263; 340/602; 177/210 FP

[56] References Cited

U.S. PATENT DOCUMENTS

| | | | |
|---|---|---|---|
| 3,260,642 | 7/1966 | Canter, Jr. | 73/73 X |
| 3,470,343 | 9/1969 | Bilbrough | 324/58.5 A |
| 3,696,292 | 10/1972 | Busker et al. | 324/58.5 A |
| 3,737,770 | 6/1973 | Masson et al. | 324/58.5 C |
| 3,739,263 | 6/1973 | Henoch | 324/58.5 C |
| 3,981,082 | 9/1976 | Massey | 324/58.5 A |
| 4,123,702 | 10/1978 | Kinanen et al. | 324/58.5 A |

OTHER PUBLICATIONS

Publ. "Application of On-Line Microwave Moisture Gauge at Wet End", Richard A. Reese, pp. 54–57, Paper Trade Journal 9/11/72.

Primary Examiner—Daniel M. Yasich
Attorney, Agent, or Firm—Schwartz, Jeffery, Schwaab, Mack, Blumenthal & Koch

[57] ABSTRACT

An apparatus for measuring the percentage of moisture content and weight of a sheet-like object has a pair of metal boxy sections for providing a cavity resonator with openings, defining a gap interposed therebetween. In measurement, the sheet-like object is inserted in the gap. The percentage of moisture content of the sheet-like object is measured by detecting the variable resonant voltage of a microwave signal introduced into the cavity resonator. Weighing of the sheet-like object is measured detecting the variable resonant frequency of the microwave signal introduced.

10 Claims, 8 Drawing Figures

APPARATUS FOR MEASURING A PERCENTAGE OF MOISTURE AND WEIGHING OF A SHEET-LIKE OBJECT

BACKGROUND OF THE INVENTION

The present invention relates to an apparatus for measuring the percentage of moisture content and the weight of a sheet-like object. The object is inserted into a cavity resonator and a percentage of moisture content of the sheet-like object is measured by detecting a variable and attenuated resonant voltage of a microwave introduced into the cavity resonator. Further, the weight of the sheet-like object is measured by detecting a variable resonant frequency of the microwave introduced.

Typically, separate measuring system are used for measuring the moisture content or percentage of moisture content and the weight per unit area of sheet-like objects for indicating the quality of the objects. For example, to measure the percentage of moisture, infrared rays or microwaves are used to irradiate an object to be measured and the amount of the attenuated wave is measured. To measure weighing, $\beta$ rays or X rays are used to irradiate the object and an amount of the rays transmitted through the object is measured.

As described above, the conventional measuring apparatus of this type needs two independent measuring systems with different irradiating sources, so that the measuring apparatus is bulky and expensive. Because of use of $\beta$ or X rays is hazardous to the human body, the conventional measuring apparatus further needs protective devices for protecting the human body from exposure. The use of two measuring systems further makes it difficult to measure a paper making process in an on-line manner.

SUMMARY OF THE INVENTION

Accordingly, an object of the invention is to provide an apparatus for measuring the percentage of moisture content and the weight of a sheet-like object with a microwave source which is used for both measurements.

To achieve this object, there is provided an apparatus for measuring the percentage of moisture content and the weight of a sheet-like object comprising: a cavity resonator with a gap permitting a sheet-like object to be inserted thereinto; microwave guide means for guiding a microwave into the cavity resonator by making the microwave pass therethrough; means for producing detected output signals at a resonance dependent upon the sheetlike object inserted into the cavity resonator for measurements; and means for measuring a percentage of moisture of the sheet-like object on the basis of a resonant voltage attenuated of a detected output signal and for measuring a weighing of the sheet-like object on the basis of resonant frequency of a detected output signal.

With such an arrangement, a microwave generated from a microwave oscillator may be used as a common irradiating source for both the measurements of the percentage of moisture and the weighing of the sheet-like object inserted in the cavity resonator. Therefore, both the measurements of the sheet like object may be made by an identical measuring system, without using $\beta$ rays or X rays hazardous to the human body. Accordingly, the measuring apparatus may be made small in size. Further, such an arrangement enables the paper manufacturing process to be measured an on-line manner.

BRIEF DESCRIPTION OF THE DRAWINGS

The invention will be better understood upon reading the following description in connection with the accompanying drawings, in which.

DETAILED DESCRIPTION OF THE PREFERRED EMBODIMENTS

Figure 1:
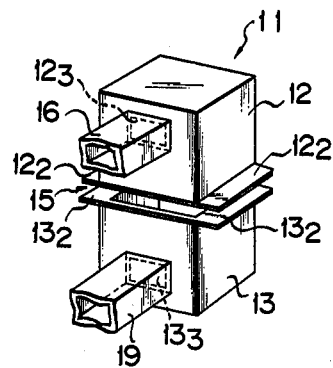
FIG. 1 shows a perspective view of a cavity resonator which is an embodiment according to the invention.
Figure 2:
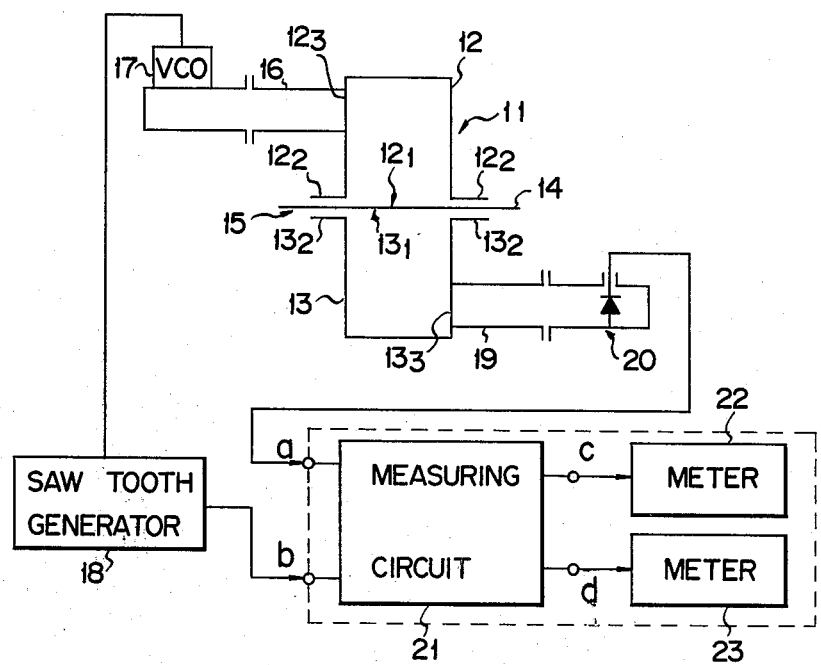
FIG. 2 shows a block diagram of a measurement system which is an embodiment according to the invention.

Referring now to the drawings and particularly FIGS. 1 and 2, a cavity resonator 11 which is an embodiment according to the invention is comprised of upper and lower metal boxy sections 12 and 13 for providing cavities with openings $12_1$ and $13_1$ arranged facing each other with gap 15 intervening therebetween. In measurement, a sheet-like object 14 to be measured is inserted into the gap 15. A flange $12_2$ provided at the opening $12_1$ of the upper section 12 and a flange $13_2$ provided at the opening $13_1$ of the lower section 13 are capacitively coupled with each other. One side of the upper section 12 is opened to have a coupling hole $12_3$ coupled with a wave guide 16. A microwave oscillator 17 such as VCO (voltage controlled oscillator) is mounted to the wave guide 16. The VCO 17 is connected to a saw-tooth wave oscillator 18 whereby a saw-tooth wave is applied to the oscillator 18 to oscillate a microwave signal which in turn is guided through the wave guide 16 to the cavity resonator 11. The lower section 13 is opened at one side to have a coupling hole $13_3$ coupled with a wave guide 19. Within the wave guide 19, a device to detect a resonant output signal of the resonator 11, for example, a diode detector 20, is provided. An output signal from the detector 20 is applied from a terminal a to a measuring circuit 21. The measuring circuit 21 receives the detected output from the detector 20 and produces at an output terminal c a resonant voltage dependent on the sheet-like object inserted into the gap 15 of the resonator 11. The resonant voltage is then applied to a meter 22 where it is visually indicated. The measuring circuit 21 also receives the saw-tooth wave signal from the saw-tooth wave oscillator 18 to produce a resonant frequency dependent on the sheetlike object at an output terminal d. The resonant frequency is then applied to a meter 23 where it is visually indicated.

Figure 3:
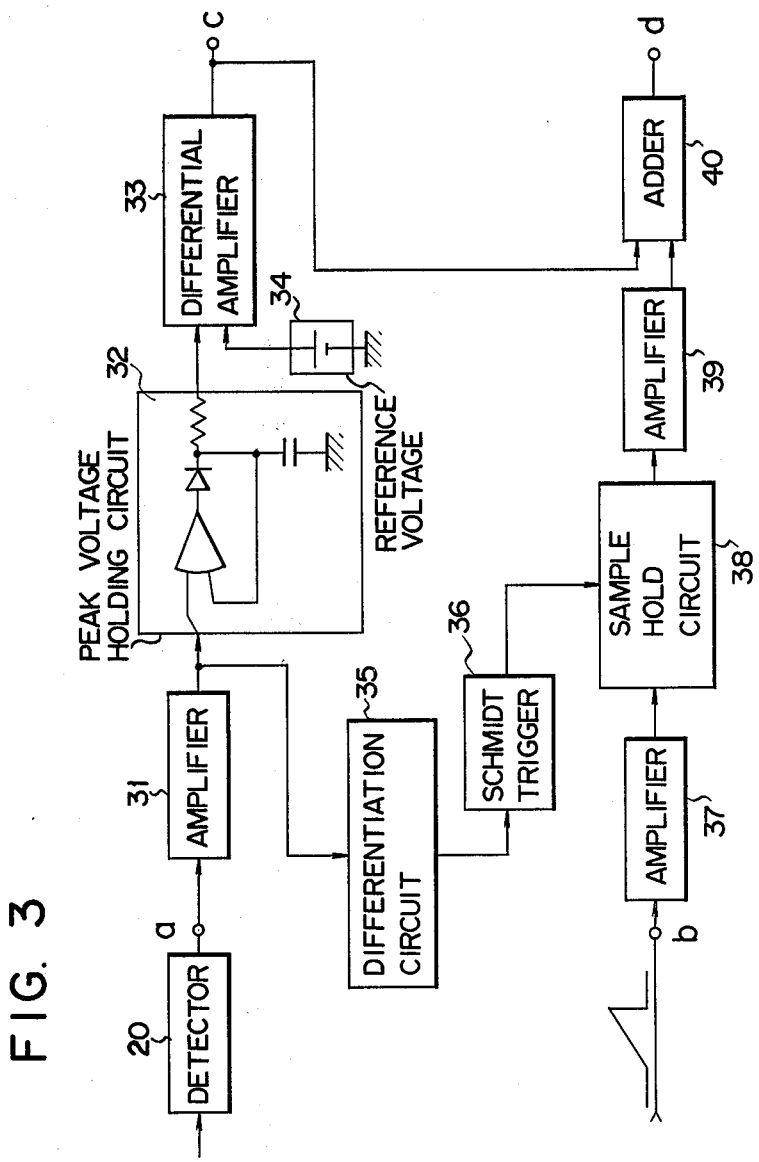
FIG. 3 shows a block diagram of an embodiment of the measurement system shown in FIG. 2.

The detailed circuit diagram of the measuring circuit 21 will be described with reference to FIG. 3. All of the circuit elements in FIGS. 2 and 3 are conventional elements, easily obtainable and well known in the art. The detected output signal from the detector 20 is inputted through the terminal a to an amplifier 31 of which the output signal is then applied to a known peak voltage hold circuit 32 which holds a peak value of the resonant voltage dependent on the object. The peak voltage is then compared with a reference voltage 34 in a differential amplifier 33. The output signal from the differential amplifier 33 is provided at a terminal c. The output signal from the amplifier 31 is applied to a differentiation circuit 35 where it is differentiated to produce a differentiated waveform signal which in turn is inputted to a Schmidt trigger circuit 36. Upon receipt of the differential signal, the Schimdt trigger circuit 36 produces a rectangular wave signal. A saw-tooth wave signal inputted through the terminal b is inputted through an amplifier 37 to a sample hold circuit 38. Upon receipt of the rectangular wave signal derived from the Schimdt trigger circuit 36, the sample hold circuit 38 sweeps the saw-tooth wave signal to produce an output signal proportional to the resonant frequency of the signal of those detected output signals. The output signal from the sample hold circuit is applied through an amplifier 39 to an adder 40. Applied to the adder 40, a resonant voltage derived from the differential amplifier 33 is compared with the output signal proportional to the resonant frequency to compensate for a deviation of the moisture content to the resonant frequency value at the resonant voltage. The compensated voltage is outputted from a terminal d.

Figure 4:
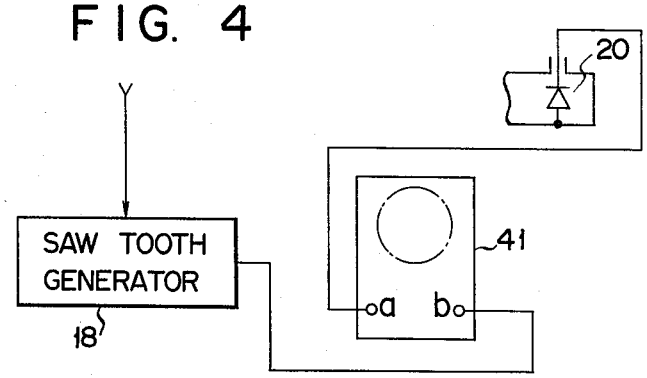
FIG. 4 shows a block diagram of another embodiment in place of the measuring circuit and meters shown in FIG. 2.

In place of the measuring circuit 21 and the meters 22 and 23, an oscilloscope 41 may be used as shown in FIG. 4. In this case, the output signal from the detector 20 is applied as a vertical input signal to a terminal a of the oscilloscope 41. On the other hand, a saw-tooth wave signal from the saw-tooth wave oscillator 18 is supplied as a horizontal input signal to a terminal b. As a result, a resonant curve dependent on the object to be measured is depicted on the display surface and from the curve depicted, the resonant voltage and the resonant frequency may be measured.

Figure 5:
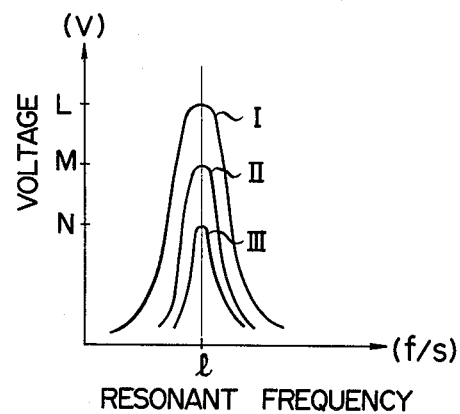
FIG. 5 shows characteristic curves of resonant voltage values with respect to a resonant frequency when a percentage of moisture content of a sheet-like object changes.

By using the above-mentioned measuring circuit 21 or the oscilloscope 41, the object 14 is inserted into the gap 15 of the cavity resonator 11 and the saw-tooth wave voltage from the saw-tooth-wave oscillator 18 is applied to the VCO 17. Upon application thereto of the sawtooth wave, the VCO 17 produces a microwave signal frequency-modulated in accordance with the level of the applied voltage which in turn is led to the cavity resonator 11 by way of the wave guide 16. When the oscillating frequency introduced approaches the resonant frequency of the cavity resonator 11, the resonant output is guided out to the detector 20 through the wave guide 19. In this case, if the object 14 has a given weight, and the resonant voltage value and the resonant frequency are L(V) and l(f/s), a resonant curve is depicted as indicated by curve I in FIG. 5. As the moisture content contained in the object with the given weight increases, an attenuation of the microwave increases, so that the resonant voltage decreases from L(V) to M(V) and the resonant curve changes to become a curve II. When the moisture content further increases, the resonant voltage decreases from M(V) to N(V) and the resonant curve becomes a curve III.

Figure 6:
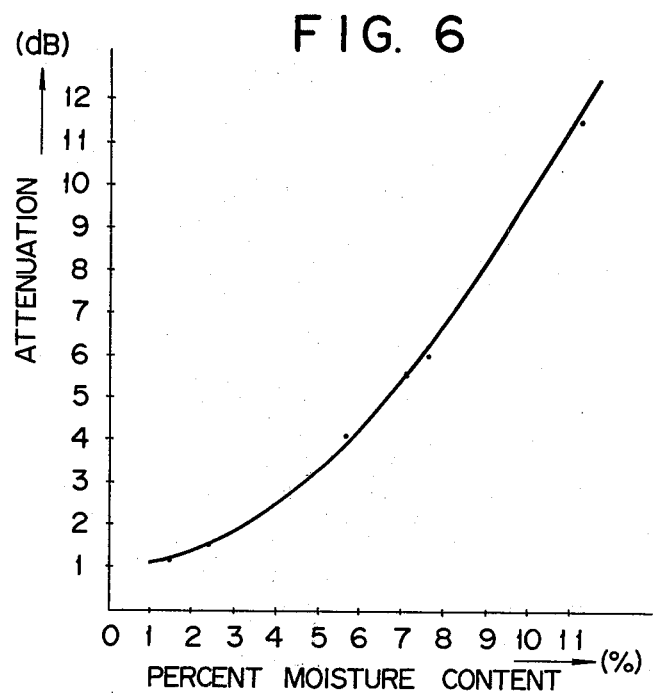
FIG. 6 shows a characteristic curve of the resonant voltages with respect to the resonant frequency when the weight of an object to be measured inserted within the cavity resonator changes under a fixed percentage of moisture content.

A relation between a percentage of the content of the water contained in the object to be measured and an attenuation of the microwave transmitted therethrough is as shown in FIG. 6, as a result of the measurement. As seen from the figure, the attenuation substantially linearly changes with increase of the moisture content. Therefore, by measuring the microwave resonant voltage by using the measuring circuit 21 or the oscilloscope 41 and measuring the attenuation of the microwave, a percentage of moisture content substantially proportional to the attenuation may be obtained.

Figure 7:
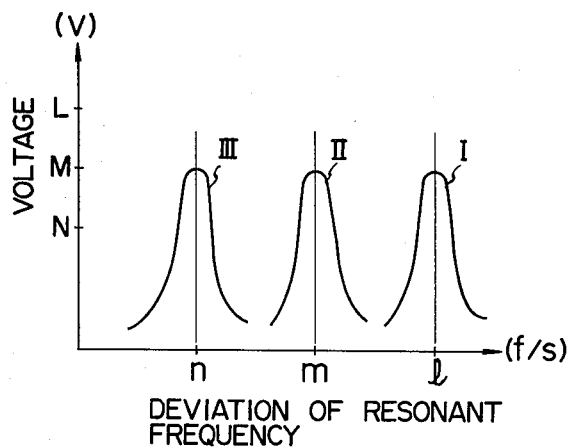
FIG. 7 shows characteristic curves of a percentages of moisture content with respect to an amount of attenuated microwave obtained by using a measuring apparatus according to the present invention.

Curve I of FIG. 7 shows the resonance curve for object 14 which contains water with a given percent of moisture content, the resonant voltage is M(V) and the amount of frequency deviation from the resonant frequency detected when no object is inserted in the gap of the cavity resonator is l(f/s). When the weight of object 14 having a given percent of moisture content changes, the resonant frequency decreases to be m(f/s) (l>m) and the resonant curve changes to become a curve II. When the weight increases, a deviation of the resonant frequency decreases from m(f/s) to n(f/s), and its resonant curve is depicted as a curve III.

Figure 8:
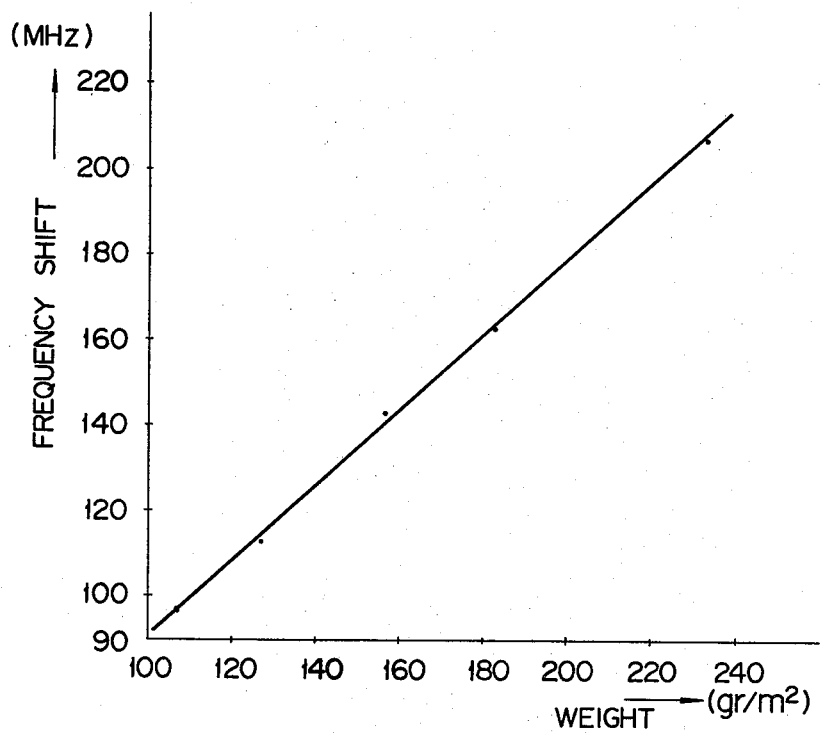
FIG. 8 shows a characteristic curve of weight to resonant frequency shift with respect to the weight obtained by using a measuring apparatus according to the invention.

The experiment showed a relation between a weight of the object and the resonant frequency detected as shown in FIG. 8. As shown, the resonant frequency substantially linearly changes as the weight increases. Accordingly, by measuring a deviation of the resonant frequency by means of the measuring circuit 21 or the oscilloscope 41, a weight proportional to the resonant frequency displacement may be obtained.

Having described a specific embodiment of the invention, it is obvious that modification and variation of the invention is possible in light of the above teachings.

What is claimed is:

1. Apparatus for measuring the moisture content and weight of a sheet-like object comprising:
   (a) a single cavity resonator having a pair of metal boxy sections with openings arranged spaced from and facing each other thereby providing a gap therebetween for insertion of said sheet-like object,
   (b) means for generating microwave signals,
   (c) means for coupling said microwave signals to one of said metal boxy sections,
   (d) a microwave detector,
   (e) means for coupling microwave signals from the other of said metal boxy sections to the detector, said coupled microwave signals being attenuated and shifted in frequency at a resonance condition of said cavity resonator when said sheet-like object is inserted within said gap,
   (f) said detector generating resonance signals upon detection of a resonance condition, and
   (g) circuit means connected to said detector for receiving said resonance signals, said circuit means comprising
      (1) means for detecting the amount of attenuation of said resonance signals for substantially determining the moisture content of said sheet-like object, and
      (2) means for detecting the resonance frequency of said resonance signals for determining the weight of said sheet like object.

2. Apparatus as recited in claim 1, wherein said means for coupling said microwave energy to said one of said metal boxy sections includes a first microwave guide means, said microwave generating means mounted to said first microwave guide means.

3. Apparatus as recited in claim 2, wherein said microwave generating means comprises a saw-tooth generator.

4. Apparatus as recited in claims 2 or 3, wherein said microwave generating means comprises a voltage controlled oscillator.

5. Apparatus as recited in claim 1, wherein said means for coupling microwave signals to said detector comprises a second microwave guide means, said detector mounted within said second microwave guide means.

6. Apparatus as recited in claim 5, wherein said detector comprises a diode detector.

7. Apparatus as recited in claim 1, wherein said means for detecting the amount of attenuation of said resonance signals comprises:
   a peak voltage holding circuit for determining the peak voltage of said resonance signals,
   a reference voltage source for generating a reference voltage, and
   comparator means for comparing said peak voltage with said reference voltage, said comparator means providing an output signal indicative of moisture content, and
   said apparatus further comprising indication means responsive to said moisture content output signal for indicating same.

8. Apparatus as recited in claim 7, wherein said comparator means comprises a differential amplifier.

9. Apparatus as recited in claims 1 or 7, wherein said means for generating microwave signals comprises a sawtooth generator and voltage controlled oscillator, and wherein said means for detecting the resonance frequency of said resonance signals comprises:
   a differentiation circuit for receiving and differentiating said resonance signals,
   a sample and hold circuit connected to receive the output of said differentiation circuit, and an output of said saw-tooth generator,
   an amplifier connected to receive the output of said sample and hold circuit,
   an adder circuit connected to receive the output of said amplifier and said attenuating detecting means for adding same, and
   indicating means for indicating the resonance frequency of said resonance signals.

10. Apparatus as recited in claim 1, wherein said means for generating microwave signals comprises a saw-tooth generator and a voltage controlled oscillator, and said circuit means comprises an oscilloscope connected to receive said resonance signals as a vertical input thereto and connected to receive a saw-tooth voltage from said saw-tooth generator as a horizontal input thereto, whereby said oscilloscope displays a resonance curve of said attenuated, frequency-shifted resonance signals.

* * * * *